(12) United States Patent
Bunick et al.

(10) Patent No.: US 8,173,161 B2
(45) Date of Patent: May 8, 2012

(54) METHOD OF ADMINISTERING A PHARMACEUTICAL ACTIVE INGREDIENT

(75) Inventors: Frank J. Bunick, Randolph, NJ (US); Feng Lin, San Antonio, TX (US)

(73) Assignee: McNeil-PPC, Inc., Skillman, NJ (US)

(*) Notice: Subject to any disclaimer, the term of this patent is extended or adjusted under 35 U.S.C. 154(b) by 144 days.

(21) Appl. No.: 12/370,117

(22) Filed: Feb. 12, 2009

(65) Prior Publication Data
US 2009/0258039 A1    Oct. 15, 2009

Related U.S. Application Data

(63) Continuation of application No. 10/309,730, filed on Dec. 4, 2002, now abandoned.

(51) Int. Cl.
*A61K 9/20* (2006.01)
(52) U.S. Cl. .................................................. 424/464
(58) Field of Classification Search .................. None
See application file for complete search history.

(56) References Cited

U.S. PATENT DOCUMENTS

| | | |
|---|---|---|
| 3,146,169 A | 8/1964 | Stephenson et al. |
| 3,851,638 A | 12/1974 | Alexander |
| 4,209,513 A | 6/1980 | Torode et al. |
| 4,327,076 A | 4/1982 | Puglia et al. |
| 4,395,422 A | 7/1983 | Schmidt et al. |
| 4,507,511 A | 3/1985 | Reiff et al. |
| 4,533,674 A | 8/1985 | Schmidt et al. |
| 4,562,024 A | 12/1985 | Rogerson |
| 4,631,284 A | 12/1986 | Salpekar et al. |
| 4,661,647 A | 4/1987 | Serpelloni et al. |
| 4,663,147 A | 5/1987 | DePrince |
| 4,710,519 A | 12/1987 | Finnan et al. |
| 4,803,076 A | 2/1989 | Ranade |
| 4,812,316 A | 3/1989 | Rossi et al. |
| 4,814,179 A | 3/1989 | Bolton et al. |
| 4,816,262 A | 3/1989 | McMullen |
| 4,820,524 A | 4/1989 | Berta |
| 4,839,177 A * | 6/1989 | Colombo et al. ............ 424/482 |
| 4,851,226 A | 7/1989 | Julian et al. |
| 4,904,477 A | 2/1990 | Ho et al. |
| 4,906,478 A | 3/1990 | Valentine et al. |
| 4,983,399 A | 1/1991 | Maish |
| 5,075,114 A | 12/1991 | Roche |
| 5,104,648 A | 4/1992 | Denton et al. |
| 5,178,878 A | 1/1993 | Wehling et al. |
| 5,204,115 A | 4/1993 | Olinger et al. |
| 5,217,965 A | 6/1993 | Oshlack et al. |

(Continued)

FOREIGN PATENT DOCUMENTS

CA    1 229 552    11/1987

(Continued)

OTHER PUBLICATIONS

Remington: The Science and Practice of Pharmacy, p. 208-09 (2000).

(Continued)

*Primary Examiner* — Bethany Barham

(57) ABSTRACT

A method for reducing the friability of soft substrates by applying an effective amount of a water soluble, polymeric dispersion to at least a portion of a treatment surface of the substrate, such that less than about 90% of the exterior surface has the dispersion applied thereto.

19 Claims, 8 Drawing Sheets

U.S. PATENT DOCUMENTS

| | | | |
|---|---|---|---|
| 5,223,264 A | 6/1993 | Wehling et al. | |
| 5,262,171 A | 11/1993 | Login et al. | |
| 5,275,822 A | 1/1994 | Valentine et al. | |
| 5,320,848 A | 6/1994 | Geyer et al. | |
| 5,464,632 A | 11/1995 | Cousin et al. | |
| 5,489,436 A | 2/1996 | Hoy et al. | |
| 5,490,987 A | 2/1996 | Shen et al. | |
| 5,556,639 A * | 9/1996 | Fielden | 424/480 |
| 5,573,777 A | 11/1996 | Serpelloni et al. | |
| 5,674,529 A | 10/1997 | Marder et al. | |
| 5,728,400 A | 3/1998 | Battist et al. | |
| 5,846,568 A | 12/1998 | Olinger et al. | |
| 5,869,102 A | 2/1999 | Stroppolo et al. | |
| 5,879,706 A | 3/1999 | Carter et al. | |
| 5,888,548 A | 3/1999 | Wongsuragral et al. | |
| 5,922,342 A | 7/1999 | Shah et al. | |
| 6,103,260 A | 8/2000 | Luber et al. | |
| 6,110,500 A | 8/2000 | Kim | |
| 6,210,710 B1 | 4/2001 | Skinner | |
| 6,258,381 B1 | 7/2001 | Luber et al. | |
| 6,270,790 B1 * | 8/2001 | Robinson et al. | 424/441 |
| 6,274,162 B1 | 8/2001 | Steffenino et al. | |
| 6,277,409 B1 | 8/2001 | Luber et al. | |
| 6,468,563 B1 | 10/2002 | Schmidt et al. | |
| 6,713,089 B1 | 3/2004 | Bertelsen et al. | |
| 2003/0124183 A1 | 7/2003 | Sowden | |

FOREIGN PATENT DOCUMENTS

| | | |
|---|---|---|
| EP | 0 070 127 A2 | 1/1983 |
| EP | 0 487 774 B1 | 6/1992 |
| EP | 0 284 849 B1 | 8/1993 |
| EP | 0 913 148 A1 | 5/1999 |
| EP | 0 933 079 A1 | 8/1999 |
| FR | 2 790 387 A1 | 3/1999 |
| GB | 1 533 243 A | 11/1978 |
| GB | 2 305 604 A | 4/1997 |
| RU | 2 039 553 C1 | 7/1995 |
| WO | WO 93/13758 A1 | 7/1993 |
| WO | WO 97/07822 A1 | 3/1997 |
| WO | WO 97/38678 A1 | 10/1997 |
| WO | WO 97/48383 A1 | 12/1997 |
| WO | WO 98/20858 A1 | 5/1998 |
| WO | WO 98/46215 A1 | 10/1998 |
| WO | WO 9846215 A1 | 10/1998 |
| WO | 9917771 A1 | 4/1999 |
| WO | WO 99/15155 A1 | 4/1999 |
| WO | WO 99/17766 A1 | 4/1999 |
| WO | WO 99/17771 A1 | 4/1999 |
| WO | WO 99/18937 A1 | 4/1999 |
| WO | WO 9930689 A1 | 6/1999 |
| WO | WO 99/32090 A1 | 7/1999 |
| WO | WO 9932092 A1 | 7/1999 |
| WO | WO 03/007918 | 1/2003 |
| WO | WO 03/072086 A1 | 9/2003 |

OTHER PUBLICATIONS

Lieberman et al., "Pharmaceutical Dosage Forms—Tablets," vol. (2) (1990) p. 213-17, 327-329.

Lachman et al., "The Theory and Practice of Industrial Pharmacy," (Ch. 11) ($3^{rd}$ Ed. 1986).

USP 23, Ch <1216> p. 1981 (1995).

The Elizabeth Companies Tablet Design Training Manual (p. 7) (Available as early as Sep. 27, 2002).

USP 24, 2000 Version, 19-20 and 856 (1999).

Introduction to Phoqus, Oct. 3, 2003.

EP Search Report for 03 25 7620 dated Mar. 9, 2004.

* cited by examiner

METHOD OF ADMINISTERING A PHARMACEUTICAL ACTIVE INGREDIENT

CROSS REFERENCE TO RELATED APPLICATION

This is a continuation of prior U.S. application Ser. No.10/309,730, filed Dec. 4, 2002 now abandoned, which is incorporated by reference in its entirety herein.

FIELD OF THE INVENTION

This invention relates to a surface treatment composition for soft substrates, and methods for preparing and applying the same.

BACKGROUND OF THE INVENTION

Soft dosage forms are widely used in a variety of consumer products. For example, many soft confections have been marketed with commercial success due to consumer preference. Further, pharmaceutical manufacturers have also developed oral dosage forms that provide alternatives to the traditional, swallowable solid tablets. These alternative dosage forms, which for example include chewable or orally disintegrable tablets, are often easier and more convenient to administer, especially to pediatric and geriatric patients. Softer tablets are also advantageous for applications where it is desirable to provide for the topical availability of an active ingredient in the mouth or throat to provide either local effects or systemic absorption.

In chewable dosage forms, active ingredients are often employed in the form of particles that are coated with tastemasking polymers. Such dosage forms, which possess an easier "bite-through" and superior tastemasking performance, are prepared by employing reduced compaction pressures during manufacture. Although the resulting dosage forms are generally softer, they also are disadvantageously more fragile, brittle, and thus more easily chipped. This increased fragility, or friability of soft tablets adds cost and complexity to handling and packaging of these dosage forms.

In disintegratable dosage forms, the dosage form is designed to disintegrate in the mouth without chewing. See, e.g., U.S. Pat. Nos. 5,464,632, 5,223,264 and 5,178,878. While these soft tablets advantageously disintegrate completely in the mouth prior to swallowing, they also have the disadvantage of being highly friable. Thus, this dosage form also requires costly specialized handling and packaging in order to prevent breakage.

Known methods for reducing the friability of soft chewable or disintegrable tablets include incorporation of low-melting materials in the tablet matrix. PCT Application No. WO 93/13758, for example, describes soft tablets comprising a meltable binder distributed throughout the tablet, which has been melted and solidified to improve the strength (e.g. hardness and friability) of the tablets. U.S. Pat. No. 4,327,076 discloses a soft, breakage-resistant chewable tablet compressed from particles comprising a fatty material. U.S. Pat. No. 6,258,381 describes a tablet made from a granular agglomerate comprising a mixture of at least one active ingredient and a binder. After the granular agglomerate is heated to melt the binder only at or near the tablet surface it is then cooled in order to solidify the melted binder into a substantially continuous phase. This results in the formation of a fused layer on the outside of the tablet, which reduces its friability. U.S. Pat. No. 6,277,409 describes a soft chewable tablet coated with a molten material, which is then solidified to form a protective coating that reduces the friability of the soft tablet. Although these processes yield tablets having the consumer-preferred soft tablet core and reduced friability, the high levels of coating material employed are economically disadvantageous.

Swallowable tablets are commonly coated with film coatings or polymeric coatings, such as those comprising cellulose derivatives, in order to improve their swallowability. These coatings typically surround the entire surface of the tablet. However, the coatings typically employed for swallowable tablets are not particularly suitable for use on chewable tablets or those designed to disintegrate in the oral cavity because they would hinder the dissolution, disintegration, chewability, and organoleptic characteristics, such as mouthfeel of such soft tablets.

It is also known in the art to apply an impermeable coating on only a portion of the dosage form for the purpose of controlling the surface area through which active ingredient is released from the dosage form. See, e.g. U.S. Pat. No. 5,922,342. According to one embodiment of this method, a desired modified, controlled, or substantially constant, or "zero-order", dissolution rate is provided on the tablets by controlling the surface area of contact between the core and dissolution medium. See for example, U.S. Pat. Nos. 3,146,169; 3,851,638; 4,663,147; 4,816,262; and 6,110,500. Typical manufacturing methods for these types of dosage forms include making a core, coating the core with impermeable material, then removing a portion of the core and coating to create the area for drug dissolution. See, e.g., U.S. Pat. No. 4,803,076 (tablet press for use in the manufacture of a truncated cone-shaped, as well as an apparatus for removal of a portion of the coated dosage form). Generally, a substantial level of coating is required in these types of controlled release applications in order for the coating to function as an impermeable barrier to the passage of water and/or active ingredient therethrough. Due to the dissolution rate designed for these tablets, such impermeable coatings are not only unsuitable for immediate release applications, but they are only intended for use on hard, swallowable tablets.

A need, therefore, exists for soft, immediate release tablets that have a pleasant taste as well as low friability properties, which may be processed with standard bulk handling equipment and packaged in bottles.

SUMMARY OF THE INVENTION

The present invention comprises, consists of, and/or consists essentially of a treated pharmaceutical substrate comprised of, consisting of, and/or consisting essentially of:

a) a soft pharmaceutical substrate having a hardness value of no more than about 15 kp/cm$^2$ and comprised of an exterior surface having an exterior surface area, said exterior surface comprised of at least one treatable surface; and b) a pharmaceutically-acceptable, water dispersible polymer layer in contact with at least a portion of said treatable surface to form a treated surface, wherein said treated surface has a total surface area that is less than the total exterior surface area of the exterior surface, and the treated pharmaceutical substrate possesses a friability factor of at least about 2.

Another embodiment of the present invention is directed to a method for reducing the friability of a soft pharmaceutical substrate having a hardness value of no more than about 15 kp/cm$^2$, said soft pharmaceutical substrate comprised of an exterior surface having at least one treatable surface, comprised of, consisting of, and/or consisting essentially of:

applying an effective amount of a pharmaceutically-acceptable, water dispersible polymeric dispersion to at least a portion of said treatable surface to yield a treated pharmaceutical substrate, wherein said treatable surface has a total surface area that is smaller than the total exterior surface area of the exterior surface, and the treated pharmaceutical substrate possesses a friability factor of at least about 2.

Yet another embodiment of the present invention is directed to a treated immediate-release pharmaceutical substrate comprised of, consisting of, and/or consisting essentially of:

a) a soft pharmaceutical substrate having a hardness value of no more than about 15 kp/cm$^2$ and comprised of an exterior surface having an exterior surface area, said exterior surface comprised of at least one treatable surface; and b) a pharmaceutically-acceptable polymer layer in contact with at least a portion of said treatable surface to form a treated surface, wherein said treated surface has a total surface area that is smaller than the total exterior surface area of the exterior surface, and the treated pharmaceutical substrate possesses immediate release properties and a friability factor of at least about 2.

Yet another embodiment of the present invention is directed to a treated pharmaceutical substrate comprised of, consisting of, and/or consisting essentially of:

a) a soft pharmaceutical substrate having a hardness value of no more than about 15 kp/cm$^2$ and comprised of an exterior surface having an exterior surface area, said exterior surface comprised of at least one treatable surface; and b) a pharmaceutically-acceptable, water dispersible polymer layer in contact with at least a portion of said treatable surface to form a treated surface, wherein the weight of said water dispersible polymer layer is not more than about 0.5% of the weight of the untreated substrate, and the treated pharmaceutical substrate possesses a friability factor of at least about 2.

Advantageously the friability of the soft substrates treated in accordance with the present invention is significantly reduced without affecting their pleasant taste. Due to their reduction in friability, such treated soft substrates may be processed with standard bulk handling equipment and packaged in bottles.

DETAILED DESCRIPTION OF THE INVENTION

Figure 2A:
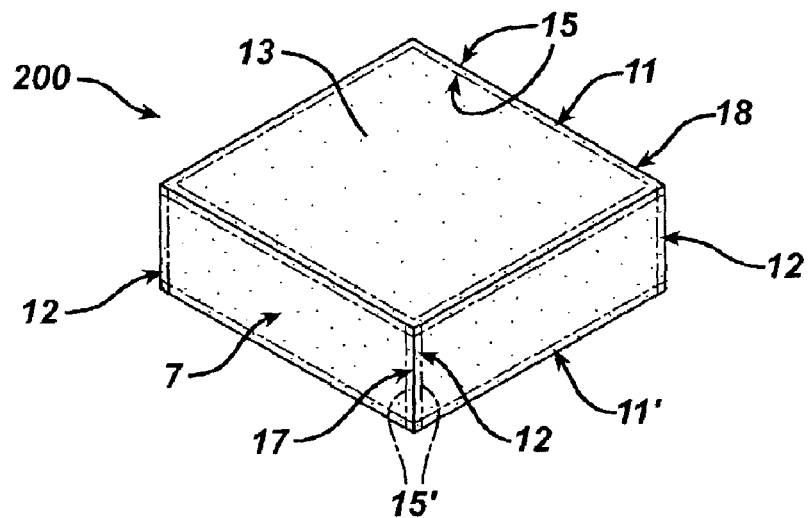
FIG. 2A is an enlarged, perspective view of a flat-faced, squared tablet.
Figure 2B:
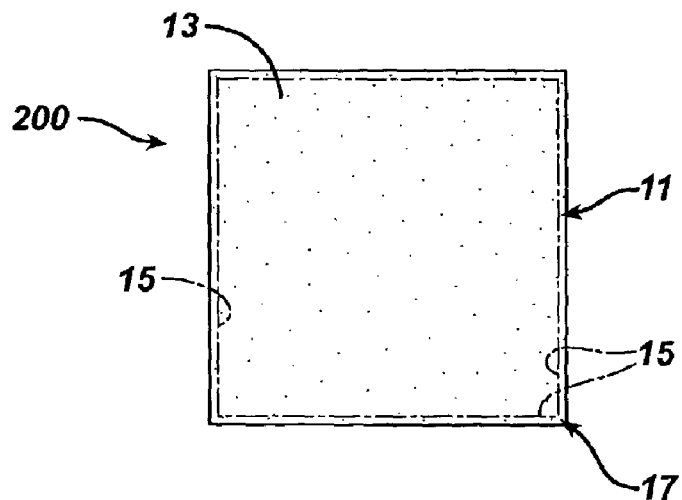
FIG. 2B is an enlarged top plan view of the tablet of FIG. 2A, the bottom plan view being identical thereto.
Figure 2C:
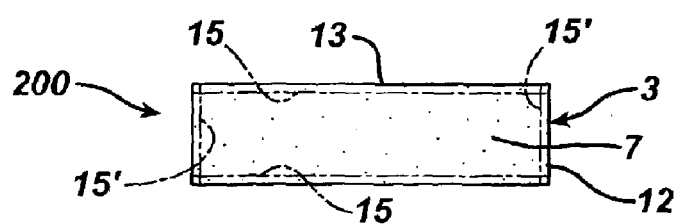
FIG. 2C is an enlarged side view of the tablet of FIG. 2A.
Figure 3A:
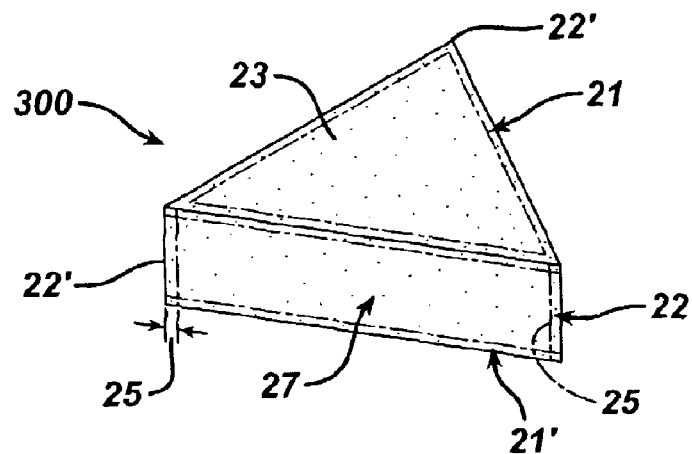
FIG. 3A is an enlarged, perspective view of a flat-faced, triangular tablet.
Figure 3B:
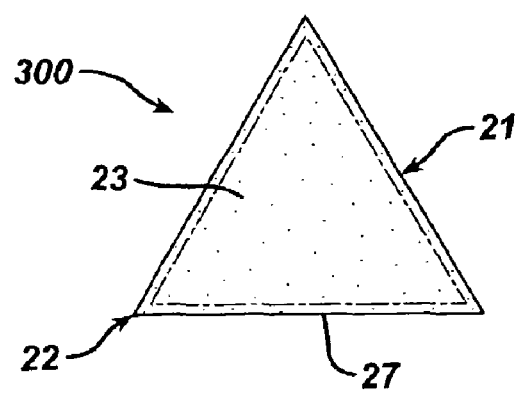
FIG. 3B is an enlarged top plan view of the tablet of FIG. 3A, the bottom plan view being identical thereto.
Figure 3C:
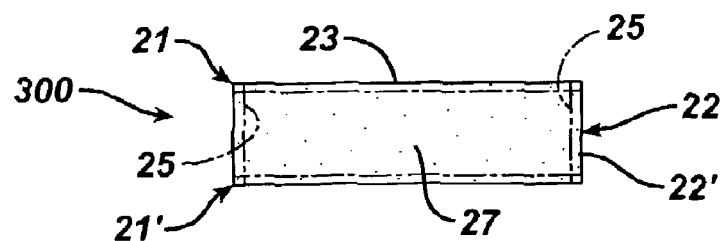
FIG. 3C is an enlarged side view of the tablet of FIG. 3A.
Figure 4A:
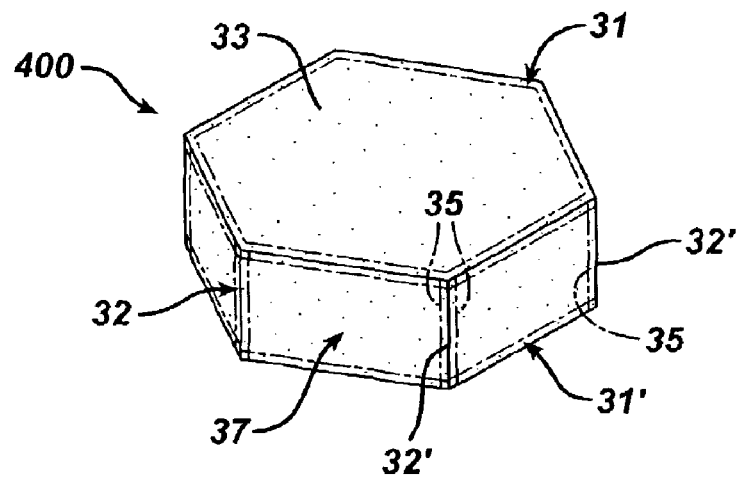
FIG. 4A is an enlarged, perspective view of a flat-faced, hexagonal tablet.
Figure 4B:
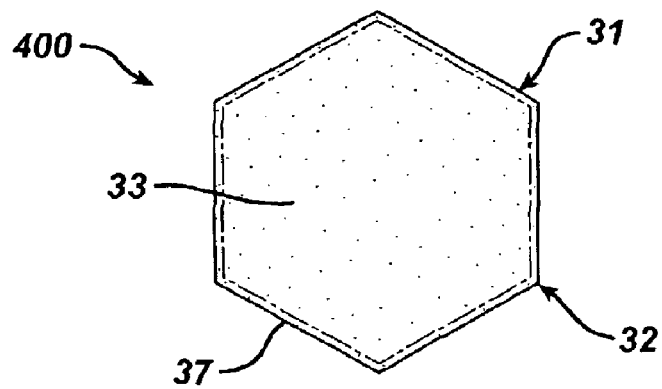
FIG. 4B is an enlarged top plan view of the tablet of FIG. 4A, the bottom plan view being identical thereto.
Figure 4C:
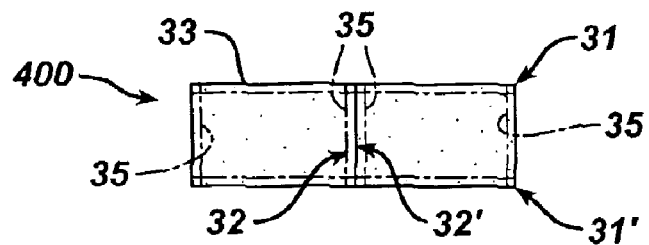
FIG. 4C is an enlarged side view of the tablet of FIG. 4A.
Figure 5A:
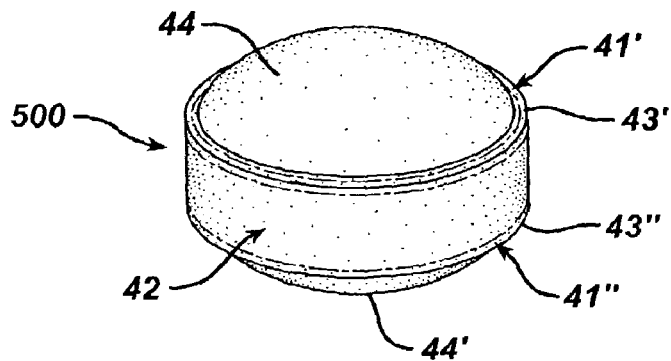
FIG. 5A is an enlarged, perspective view of a bi-convexed faced, round tablet having a ledge.
Figure 5B:
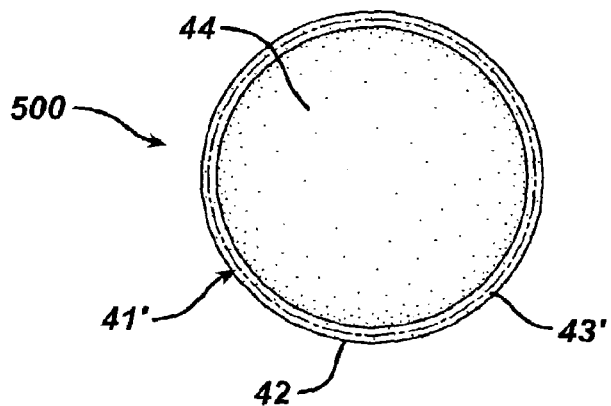
FIG. 5B is an enlarged top plan view of the tablet of FIG. 5A, the bottom plan view being identical thereto.
Figure 5C:
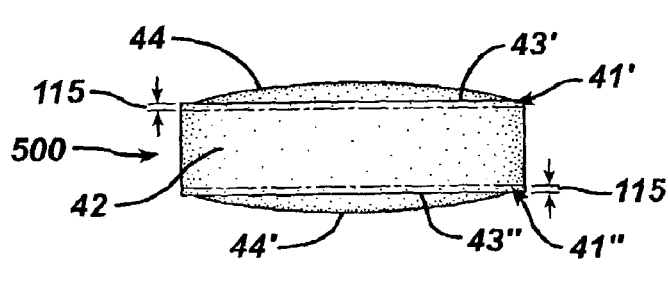
FIG. 5C is an enlarged side view of the tablet of FIG. 5A.
Figure 5D:
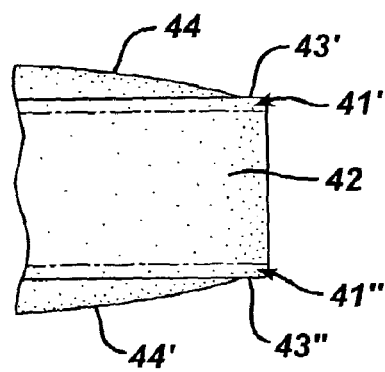
FIG. 5D is a further enlarged view of the land as illustrated in FIG. 5C.

For purposes herein the term, "substrate" refers to a surface, layer or underlying base or support upon which another substance resides or acts, and the term, "vulnerable edge" is any substrate edge, that is particularly susceptible to mechanical damage. The term, "rim," shall include a vulnerable edge on a substrate, which is defined during compaction (also referred to as "compression") via a contact region between an upper or lower punch face and a die wall, and an overlap area. "Overlap area," as used herein, shall mean a width of the substrate surface on either side of a vulnerable edge; although the size of the overlap area is not critical, it typically ranges from about 0 mm to about 2.0 mm, e.g. from about 0 mm to about 1.0 mm, in width on either side of the vulnerable edge. As illustrated in FIG. 2, the tablet possesses two rims 11, 11', each of which includes a vulnerable edge 18 and an overlap area 15 (shown in part), as well as four side vulnerable edges 12 (shown in part), each of which includes a vulnerable edge 17 and an overlap area 15'.

Figure 1A:
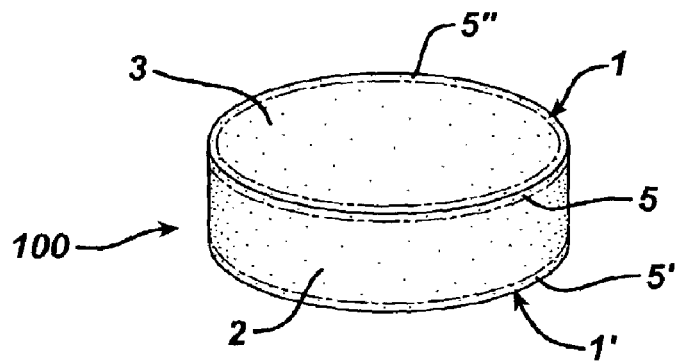
FIG. 1A is an enlarged, perspective view of a flat-faced, round tablet.
Figure 1B:
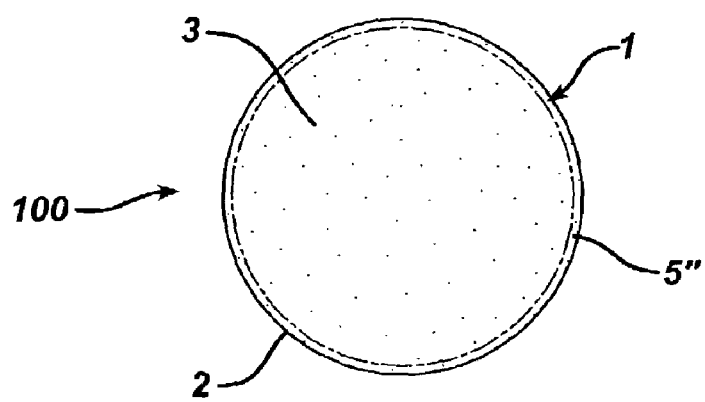
FIG. 1B is an enlarged top plan view of the tablet of FIG. 1A, the bottom plan view being identical thereto.
Figure 1C:
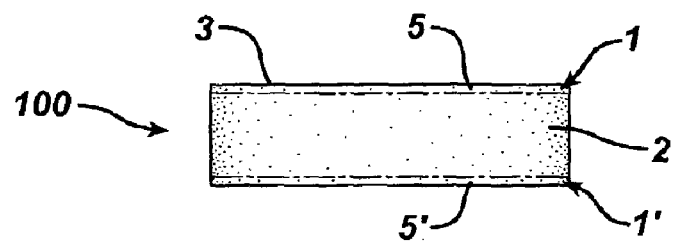
FIG. 1C is an enlarged side view of the tablet of FIG. 1A.

As illustrated in FIG. 1, "belly band," as used herein, shall mean a substrate surface 2, that is defined during compaction via contact with a die wall and includes one-half of the overlap area of the upper rim 5 and one-half of the overlap area of the lower rim 5'. "Face," as used herein, is the portion 3 of a compressed tablet formed by the upper and lower punch faces, and includes one-half of the overlap area of a rim 5". As illustrated in FIG. 5, "land," as used herein, is a planar substrate surface 43, 43' around the perimeter of a convex portion of a substrate face bearing one or more convex surfaces, and includes the rim 115. The land is formed by the perimeter of the punch face during compaction. "Treatable Surface," as used herein, shall mean any surface of the substrate that includes at least a portion of a vulnerable edge so long as the total treatable surface area is from about 10% to about 90% of the total substrate surface area. Examples of treatable surfaces include the rim, belly band, face, and/or the land, or portions thereof.

As used herein, the term "dosage form" applies to any composition designed to contain a specific pre-determined amount (dose) of a certain ingredient, such as, for example, an active ingredient as defined below. Suitable dosage forms include those suitable for oral administrations including, but not limited to, pharmaceutical drug delivery systems, or compositions for delivering minerals, vitamins and other nutraceuticals, oral care agents, flavorants, and the like.

As used herein, the term "immediate release" shall mean that the dissolution of the active ingredient contained in the dosage form conforms to USP specifications for immediate release tablets containing the particular active ingredient employed. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999).

In one embodiment, the dosage form may be an orally administered system for delivering a pharmaceutical active ingredient to the gastrointestinal tract of a human, or alternatively to the mouth or throat for localized activity, topical absorption, or systemic absorption through the oral, buccal, or pharyngeal mucosa. In another embodiment, the dosage form may be an orally administered "placebo" system consisting essentially of pharmaceutically inactive ingredients, which is designed to have the same visual appearance as a particular pharmaceutically active dosage form. Such "placebo" system dosage forms are suitable for use as control dosage forms in clinical studies, and in particular, those studies designed for testing the safety and efficacy of a particular pharmaceutically active ingredient.

"Tablets," as used herein, refer to compressed or molded solid dosage forms of any shape or size. "Water soluble" or "water solubilize," as used herein in connection with non-polymeric materials, shall mean from sparingly soluble to very soluble, i.e., not more than 100 parts water required to dissolve 1 part of the non-polymeric, water soluble solute. See Remington, "The Science and Practice of Pharmacy," pages 208-209 (2000). "Water soluble" or "water solubilize," as used herein in connection with polymeric materials, shall mean that the polymer swells in water and can be dispersed at the molecular level to form a homogeneous dispersion or colloidal solution. "Water dispersible," as used herein in connection with polymeric materials, shall mean at least a portion of the polymer is removed from the dosage form within 60 minutes after immersion of the dosage form in an aqueous medium such as that used for in-vitro dissolution testing, or gastrointestinal fluids.

"Hardness" as used herein in connection with dosage forms indicates the resistance of the dosage form to breaking in response to a diametrically applied stress. Hardness is a term used in the art to describe the diametrical breaking strength as measured by the conventional pharmaceutical hardness testing equipment, such as a Vector-Schleuniger Hardness Tester. In order to compare values across different size tablets, the breaking strength is normalized for the area of the break, which may be approximated as (tablet diameter× thickness). This normalized value, expressed in kp/cm$^2$, is sometimes referred to in the art as "tablet tensile strength." A general discussion of tablet hardness testing is found in Leiberman et al., *Pharmaceutical Dosage Forms—Tablets*, Volume 2, 2$^{nd}$ ed., Marcel Dekker Inc., 1990, pp. 213-217, 327-329, which is incorporated by reference herein.

The substrate of the present invention may be any edible solid or semi-solid composition having at least one vulnerable edge. In certain embodiments, the substrate has one or more major faces. Substrates suitable for use in the present invention may be of any size or shape. For example, in one embodiment the substrate may be in the shape of a truncated cone. In other embodiments the substrate may be shaped as a polyhedron, such as a cube, pyramid, prism, or the like; or may have the geometry of a space figure with some non-flat faces, such as a cone, cylinder, sphere, torus, or the like. Exemplary substrate shapes which may be employed include tablet shapes formed from compaction tooling shapes described by "The Elizabeth Companies Tablet Design Training Manual" (Elizabeth Carbide Die Co., Inc., p. 7 (McKeesport, Pa.) (incorporated herein by reference) as follows (the tablet shape corresponds inversely to the shape of the compaction tooling):

1. Shallow Concave.
2. Standard Concave.
3. Deep Concave.
4. Extra Deep Concave.
5. Modified Ball Concave.
6. Standard Concave Bisect.
7. Standard Concave Double Bisect.
8. Standard Concave European Bisect.
9. Standard Concave Partial Bisect.
10. Double Radius.
11. Bevel & Concave.
12. Flat Plain.
13. Flat-Faced-Beveled Edge (F.F.B.E.).
14. F.F.B.E. Bisect.
15. F.F.B.E. Double Bisect.
16. Ring.
17. Dimple.
18. Ellipse.
19. Oval.
20. Capsule.
21. Rectangle.
22. Square.
23. Triangle.
24. Hexagon.
25. Pentagon.
26. Octagon.
27. Diamond.
28. Arrowhead.
29. Bullet.
30. Barrel.
31. Half Moon.
32. Shield.
33. Heart.
34. Almond.
35. House/Home Plate.
36. Parallelogram.
37. Trapezoid.
38. Figure 8/Bar Bell.
39. Bow Tie.
40. Uneven Triangle.

Illustrative examples of some substrate shapes are shown in FIGS. 1-6. FIGS. 1A through 1C illustrate a flat-faced, round substrate 100 having an upper face 3, a lower face (not shown), an upper rim 1, a lower rim 1', and a belly band 2. FIGS. 2A through 2C illustrate a squared, flat-faced substrate 200 having an upper face 13, a lower face (not shown), a four-sided bellyband 7 (not all sides shown), four side vulnerable edges 12, an upper rim 11, and lower rim 11'. Each of the side vulnerable edges includes a vulnerable edge 17 and an overlap area 15' on each of the two adjacent bellyband sides. FIGS. 3A through 3C illustrate a triangular, flat-faced substrate 300 having an upper face 23 (one side shown), a lower face (not shown), a three-sided bellyband 27 (not all sides shown), an upper rim 21, a lower rim 21', and three side vulnerable edges 22. Each of the side vulnerable edges includes a vulnerable edge 22' and an overlap area 25 on each of the two adjacent bellyband sides. FIGS. 4A through 4C illustrate a hexagonal, flat-faced substrate having an upper face 33, lower face (not shown), a six-sided bellyband 37 (not all sides shown), upper rim 31, lower rim 31', and six vulnerable side edges 32. Each of the side vulnerable edges includes a vulnerable edge 32' and an overlap area 35 on each of the two adjacent bellyband sides. FIGS. 5A through 5D illustrate a bi-convex, round substrate 500 having an upper face 44, lower face, 44', upper rim 41', lower rim 41", bellyband 42, an upper land 43', and lower land 43".

Figure 6A:
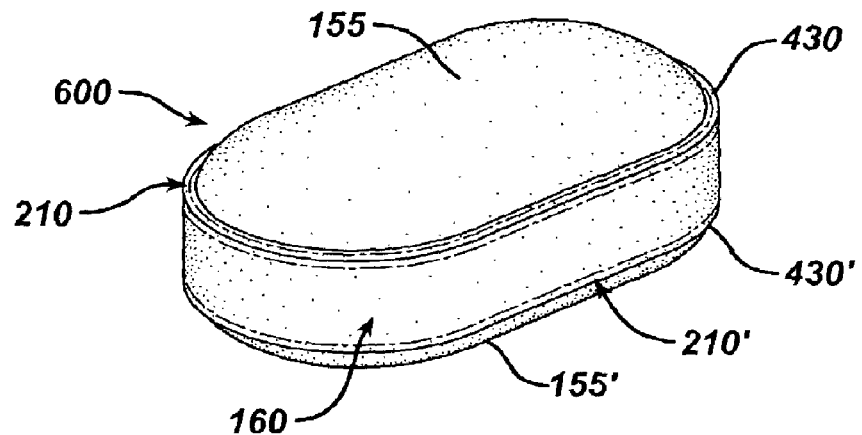
FIG. 6A is an enlarged, perspective view of a bi-convexed faced, oblong caplet.
Figure 6B:
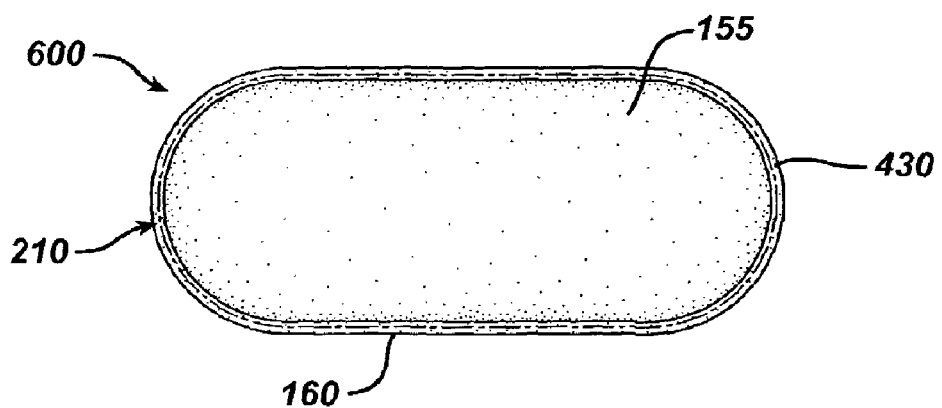
FIG. 6B is an enlarged top plan view of the caplet of FIG. 6A, the bottom plan view being identical thereto.
Figure 6C:
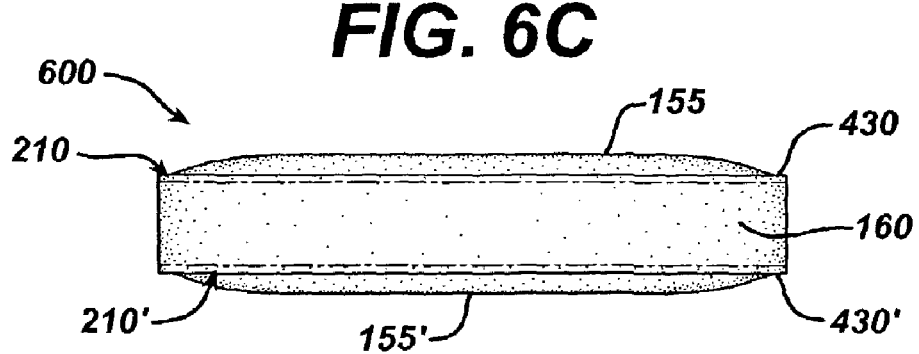
FIG. 6C is an enlarged side view of the caplet of FIG. 6A.
Figure 7A:
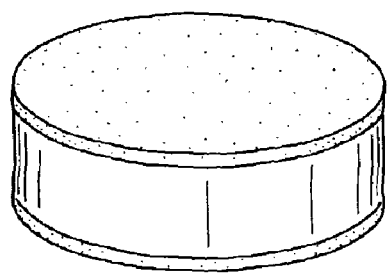
FIG. 7A is a perspective view of the tablet of FIG. 1A, having a polymeric dispersion application at both faces and both rims.
Figure 7B:
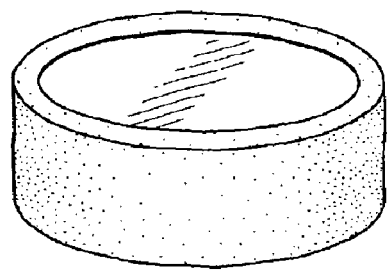
FIG. 7B is a perspective view of the tablet of FIG. 1A, having a polymeric dispersion application at the bellyband and both rims.
Figure 7C:
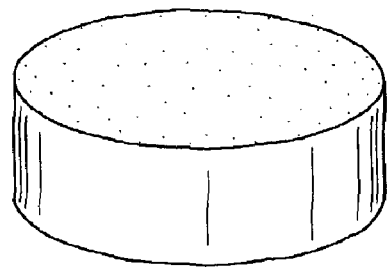
FIG. 7C is a perspective view of the tablet of FIG. 1A, having a polymeric dispersion application at the upper face and one-half of the upper rim, and at the lower face and one half of the lower rim (not shown).
Figure 7D:
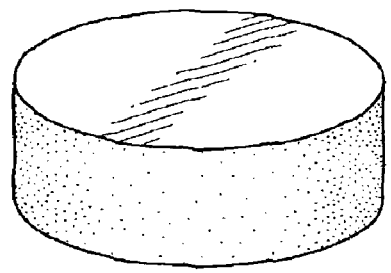
FIG. 7D is a perspective view of the tablet of FIG. 1A, having a polymeric dispersion application at the bellyband, and at one-half of the upper rim and one-half of the lower rim.
Figure 7E:
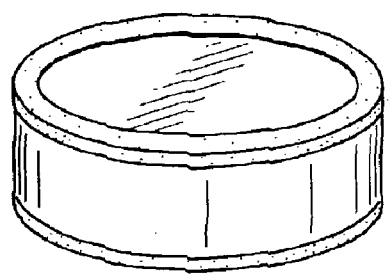
FIG. 7E is a perspective view of the tablet of FIG. 1A, having a polymeric dispersion application at both rims.

FIGS. 6A through 6C illustrate an oblong convex substrate 600 having two oppositely positioned convex faces 155, 155', and a bellyband 160 therebetween (shown most clearly in FIGS. 6A and 6C). As shown in FIG. 6A, the substrate 600 has an upper land 430, a lower land 430', an upper rim 210, and a lower rim 210'.

Substrates suitable for use in the present invention may contain one or more active ingredients. The term "active ingredient" is used herein in a broad sense and may encompass any material that can be carried by or entrained in the system. For example, the active ingredient can be a pharmaceutical, nutraceutical, vitamin, dietary supplement, nutrient, herb, foodstuff, dyestuff, nutritional, mineral, supplement, oral care agent or favoring agent or the like and combinations thereof.

Suitable oral care agents include breath fresheners, tooth whiteners, antimicrobial agents, tooth mineralizers, tooth decay inhibitors, topical anesthetics, mucoprotectants, and the like.

Suitable flavoring agents include menthol, peppermint, mint flavors, fruit flavors, chocolate, vanilla, bubblegum flavors, coffee flavors, liqueur flavors and combinations and the like.

Suitable pharmaceutical active ingredients useful herein can be selected from classes from those in the following therapeutic categories: ace-inhibitors; alkaloids; antacids; analgesics; anabolic agents; anti-anginal drugs; anti-allergy agents; anti-arrhythmia agents; antiasthmatics; antibiotics; anticholesterolemics; anticonvulsants; anticoagulants; antidepressants; antidiarrheal preparations; anti-emetics; antihistamines; antihypertensives; anti-infectives; anti-inflammatories; antilipid agents; antimanics; anti-migraine agents; antinauseants; antipsychotics; antistroke agents; antithyroid preparations; anabolic drugs; antiobesity agents; antiparasitics; antipsychotics; antipyretics; antispasmodics; antithrombotics; antitumor agents; antitussives; antiulcer agents; antiuricemic agents; anxiolytic agents; appetite stimulants; appetite suppressants; beta-blocking agents; bronchodilators; cardiovascular agents; cerebral dilators; chelating agents; cholecystekinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypoglycemic agents; ion-exchange resins; laxatives; migraine treatments; mineral supplements; mucolytics, narcotics; neuroleptics; neuromuscular drugs; non-steroidal anti-inflammatory drugs (NSAIDs); nutritional additives; peripheral vasodilators; polypeptides; prostaglandins; psychotropics; renin inhibitors; respiratory stimulants; sedatives; steroids; stimulants; sympatholytics; thyroid preparations; tranquilizers; uterine relaxants; vaginal preparations; vasoconstrictors; vasodilators; vertigo agents; vitamins; wound healing agents; and others.

In certain embodiments the active ingredient may be selected from the group of pharmaceuticals consisting of analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Examples of suitable polydimethylsiloxanes, which include, but are not limited to dimethicone and simethicone, are those disclosed in U.S. Pat. Nos. 4,906,478, 5,275,822, and 6,103,260, the contents of each is expressly incorporated herein by reference. As used herein, the term "simethicone" refers to the broader class of polydimethylsiloxanes, including but not limited to simethicone and dimethicone.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for *H. pylori*, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

In one embodiment of the invention, the gastrointestinal agents may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, the active ingredient is selected from analgesics, anti-inflammatories, and antipyretics, which included but are not limited to non-steroidal anti-inflammatory drugs (NSAIDs) including: 1) propionic acid derivatives, i.e., e.g. ibuprofen, naproxen, and ketoprofen; 2) acetic acid derivatives, i.e., e.g. indomethacin, diclofenac, sulindac, and tolmetin; 3) fenamic acid derivatives, i.e., e.g. mefanamic acid, meclofenamic acid, and flufenamic acid; 4) biphenylcarbodylic acid derivatives, i.e., e.g. diflunisal and flufenisal; and 5) oxicams, i.e., e.g. piroxicam, sudoxicam, isoxicam, and meloxicam.

In one embodiment, the active ingredient is a propionic acid derivative NSAID selected from ibuprofen, naproxen, flurbiprofen, fenbufen, fenoprofen, indoprofen, ketoprofen, fluprofen, pirprofen, carprofen, oxaprozin, pranoprofen, suprofen, and pharmaceutically acceptable salts, derivatives, and combinations thereof.

In another embodiment of the invention, the active ingredient is an analgesic selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In yet another embodiment of the invention, the active ingredient is a respiratory agent selected from pseudoephedrine, phenylpropanolamine, chlorpheniramine, dextromethorphan, diphenhydramine, astemizole, terfenadine, fexofenadine, loratadine, cetirizine, mixtures thereof and pharmaceutically acceptable salts, esters, isomers, and mixtures thereof.

Examples of particular active ingredients that may be used in the invention include, but are not limited to: acetaminophen; acetic acid; acetylsalicylic acid, including its buffered forms; acrivastine; albuterol and its sulfate; alcohol; alkaline phosphatase; allantoin; aloe; aluminum acetate, carbonate, chlorohydrate and hydroxide; alprozolam; amino acids; aminobenzoic acid; amoxicillin; ampicillin; amsacrine; amsalog; anethole; ascorbic acid; aspartame; astemizole; atenolol; azatidine and its maleate; bacitracin; balsam peru; BCNU (carmustine); beclomethasone diproprionate; benzocaine; benzoic acid; benzophenones; benzoyl peroxide; benzquinamide and its hydrochloride; bethanechol; biotin; bisacodyl; bismuth subsalicylate; bornyl acetate; bromopheniramine and its maleate; buspirone; caffeine; calamine; calcium carbonate, casinate and hydroxide; camphor; captopril; cascara sagrada; castor oil; cefaclor; cefadroxil; cephalexin; centrizine and its hydrochloride; cetirizine; cetyl alcohol; cetylpyridinium chloride; chelated minerals; chloramphenicol; chlorcyclizine hydrochloride; chlorhexidine gluconate; chloroxylenol; chloropentostatin; chlorpheniramine and its maleates and tannates; chlorpromazine; cholestyramine resin; choline bitartrate; chondrogenic stimulating protein; cimetidine; cinnamedrine hydrochloride; citalopram; citric acid; clarithromycin; clemastine and its fumarate; clonidine; clorfibrate; cocoa butter; cod liver oil; codeine and its fumarate and phosphate; cortisone acetate; ciprofloxacin HCl; cyanocobalamin; cyclizine hydrochloride; cyproheptadine; danthron; dexbromopheniramine maleate; dextromethorphan and its hydrohalides; diazepam; dibucaine; dichloralphenazone; diclofen and its alkali metal sales; diclofenac sodium; digoxin; dihydroergotamine and its hydrogenates/mesylates; diltiazem; dimethicone; dioxybenzone; diphenhydramine and its citrate; diphenhydramine and its hydrochloride; divalproex and its alkali metal salts; docusate calcium, potassium, and sodium; doxycycline hydrate; doxylamine succinate; dronabinol; efaroxan; enalapril; enoxacin; ergotamine and its tartrate; erythromycin; estropipate; ethinyl estradiol; ephedrine; epinephrine bitartrate; erythropoietin; eucalyptol; famotidine; fenoprofen and its metal salts; ferrous fumarate, gluconate and sulfate; fexofenadine; fluoxetine; folic acid; fosphenytoin; 5-fluorouracil (5-FU); fluoxetine; flurbiprofen; furosemide; gabapentan; gentamicin; gemfibrozil; glipizide; glycerine; glyceryl stearate; granisetron; griseofulvin; growth hormone; guafenesin; hexylresorcinol; hydrochlorothiazide; hydrocodone and its tartrates; hydrocortisone and its acetate; 8-hydroxyquinoline sulfate; hydroxyzine and its pamoate and hydrochloride salts; ibuprofen; indomethacin; inositol; insulin; iodine; ipecac; iron; isosorbide and its mono- and dinitrates; isoxicam; ketamine; kaolin; ketoprofen; lactic acid; lanolin; lecithin; leuprolide acetate; lidocaine and its hydrochloride salt; lifinopril; liotrix; loperamide, loratadine; lovastatin; luteinizing hormore; LHRH (lutenizing hormone replacement hormone); magnesium carbonate, hydroxide, salicylate, and trisilicate; meclizine; mefenamic acid; meclofenamic acid; meclofenamate sodium; medroxyprogesterone acetate; methenamine mandelate; menthol; meperidine hydrochloride; metaproterenol sulfate; methscopolamine and its nitrates; methsergide and its maleate; methyl nicotinate; methyl salicylate; methyl cellulose; methsuximide; metoclopramide and its halides/hydrates; metronidazole; metoprotol tartrate; miconazole nitrate; mineral oil; minoxidil; morphine; naproxen and its alkali metal sodium salts; nifedipine; neomycin sulfate; niacin; niacinamide; nicotine; nicotinamide; nimesulide; nitroglycerine; nonoxynol-9; norethindrone and its acetate; nystatin; octoxynol; octoxynol-9; octyl dimethyl PABA; octyl methoxycinnamate; omega-3 polyunsaturated fatty acids; omeprazole; ondansetron and its hydrochloride; oxolinic acid; oxybenzone; oxtriphylline; para-aminobenzoic acid (PABA); padimate-O; paramethadione; pentastatin; peppermint oil; pentaerythritol tetranitrate; pentobarbital sodium; perphenazine; phenelzine sulfate; phenindamine and its tartrate; pheniramine maleate; phenobarbital; phenol; phenolphthalein; phenylephrine and its tannates and hydrochlorides; phenylpropanolamine; phenytoin; pirmenol; piroxicam and its salts; polymicin B sulfate; potassium chloride and nitrate; prazepam; procainamide hydrochloride; procaterol; promethazine and its hydrochloride; propoxyphene and its hydrochloride and napsylate; pramiracetin; pramoxine and its hydrochloride salt; prochlorperazine and its maleate; propanolol and its hydrochloride; promethazine and its hydrochloride; propanolol; pseudoephedrine and its sulfates and hydrochlorides; pyridoxine; pyrolamine and its hydrochlorides and tannates; quinapril; quinidine gluconate and sulfate; quinestrol; ralitoline; ranitadine; resorcinol; riboflavin; salicylic acid; scopolamine; sesame oil; shark liver oil; simethicone; sodium bicarbonate, citrate, and fluoride; sodium monofluorophosphate; sucralfate; sulfanethoxazole; sulfasalazine; sulfur; sumatriptan and its succinate; tacrine and its hydrochloride; theophylline; terfenadine; thiethylperazine and its maleate; timolol and its maleate; thioperidone; tramadol; trimetrexate; triazolam; tretinoin; tetracycline hydrochloride; tolmetin; tolnaftate; triclosan; trimethobenzamide and its hydrochloride; tripelennamine and its hydrochloride; tripolidine hydrochloride; undecylenic acid; vancomycin; verapamil HCl; vidaribine phosphate; vitamins A, B, C, D, $B_1, B_2, B_6, B_{12}$, E, and K; witch hazel; xylometazoline hydrochloride; zinc; zinc sulfate; zinc undecylenate. Active ingredients may further include, but are not limited to food acids; insoluble metal and mineral hydroxides, carbonates, oxides, polycarbophils, and salts thereof; adsorbates of active drugs on a magnesium trisilicate base and on a magnesium aluminum silicate base, and mixtures thereof. Mixtures and pharmaceutically acceptable salts of these and other actives can be used.

The amount of active ingredient to be used in the substrate will depend upon several factors such as, for example, the desired active ingredient and the desired dosing requirements, and can be readily determined by one skilled in the art without undue experimentation.

Substrates suitable for use in the present invention typically include those suitable for administration as a soft dosage form, i.e. those having a hardness value that permits comfortable chewing and dissolving in the mouth. In one embodiment, the hardness of the untreated soft dosage form is no more than about 15 kiloponds per square centimeter (kp/cm$^2$), e.g., from about 1 kp/cm$^2$ to about 8 kp/cm$^2$, or from about 1 kp/cm² to about 5 kp/cm². Soft dosage forms having such low hardness values often possess a friability of more than about 2% when measured using the rotating drop method specified by the United States Pharmacopoeia 23, Chapter <1216>, p. 1981 (1995), which is incorporated by reference herein.

The substrates may be made in any manner, and for tablet dosage forms, a variety of tableting methods are known in the art. Conventional methods for tablet production include direct compression ("dry blending"), dry granulation followed by compression (i.e. compaction), and wet granulation followed by drying and compression (i.e. compaction). Other methods include the use of compacting roller technology such as a chilsonator or drop roller, or molding, casting, or extrusion technologies. All of these methods are well known in the art, and are described in detail in, for example, Lachman, et al., *The Theory and Practice of Industrial Pharmacy*, Chapter 11, (3$^{rd}$ Ed. 1986), which is incorporated by reference herein.

In the "direct compression" tableting method, a blend of the active ingredient and any other appropriate optional ingredients are directly compacted. After all ingredients are blended together, a pre-determined volume of particles from the blend is filled into a die cavity of a rotary tablet press, which continuously rotates as part of a "die table" from the filling position to a compaction position to an ejection position. At the compaction position, the particles are compacted between an upper punch and a lower punch. At the ejection position, the resulting tablet is pushed from the die cavity by the lower punch and guided to an ejection chute by a stationary "take-off" bar.

Soft substrates suitable for use in the present invention may be produced via methods known in the art such as, for example, molding or compaction. In general, soft tablets may also be made by direct compaction of a mixture of tableting ingredients, including an active ingredient, and various excipients, such as binders, flavorants, lubricants, etc. The mixture is fed into a die cavity of a tablet press and a tablet is formed by applying pressure. The hardness of the resulting soft tablet is a direct function of the compaction pressure employed and the compactability of the ingredients in the formulation, and is typically up to about 15 kiloponds per square centimeter (kp/cm².

In one embodiment of the present invention, the compressed, chewable tablet may be prepared by dry blending the active ingredient, a water-disintegratable, compressible carbohydrate such as, for example, lactose, sorbitol and/or sucrose, and other optional ingredients, then compressing the mixture into the desired shape of a dosage form having a hardness of about 1 kp/cm².

If the active ingredient has an objectionable taste, it may be coated with a known taste masking coating. Examples of suitable taste masking coatings, and methods for their production, are described in U.S. Pat. Nos. 4,851,226, 5,075,114, and 5,489,436, which are all incorporated by reference herein. Other commercially available taste masked active ingredients may also be employed. For example, acetaminophen particles which are encapsulated with ethylcellulose or other polymers by a coaccervation process may be used in the present invention. Such coaccervation-encapsulated acetaminophen may be purchased commercially from Eurand America, Inc. Vandalia, Ohio, or from Circa Inc., Dayton, Ohio.

In accordance with the present invention, a portion of the exterior surface of the substrates is treated with a polymeric dispersion. The polymeric dispersion suitable for use in the present invention is comprised of, based upon the total weight percent of the dispersion, from more than about 0% to about 25%, for example, from greater than about 0% to about 10%, from greater than about 0% to about 5%, or from greater than about 0% to about 2%, of a dispersible polymer, and from about 75% to about less than 100% of a solvent.

Dispersible polymers suitable for use in the present invention include, but are not limited to film forming polymers, gelling polymers, adhesive polymers, and derivatives, copolymers, and mixtures thereof. In one embodiment, the dispersible polymers are water soluble. The dispersible polymers are also suitable for immediate release dosage forms, which means that the dissolution of one or more active ingredients contained in dosage form conforms to USP specifications for immediate release tablets containing the particular active ingredient employed.

Examples of suitable film forming polymers for use in the present invention, include, but are not limited to, polyvinylalcohol (PVA), hydroxypropyl starch, hydroxyethyl starch, pullulan, methylethyl starch, carboxymethyl starch, methylcellulose, hydroxypropylcellulose (HPC), hydroxyethylmethylcellulose (HEMC), hydroxypropylmethylcellulose (HPMC), hydroxybutylmethylcellulose (HBMC), hydroxyethylethylcellulose (HEEC), hydroxyethylhydroxypropylmethyl cellulose (HEMPMC), methacrylic acid copolymers, methacrylate ester copolymers, polyvinyl alcohol and polyethylene glycol copolymers, proteins such as whey protein, egg albumin, casein, casein isolates, soy protein and soy protein isolates, pre-gelatinized starches, corn syrup solids, film-forming modified starches, and copolymers, derivatives and mixtures thereof. Preferred film forming polymers for use in the present invention include hydroxypropylcellulose, hydroxypropylmethylcellulose, and copolymers and mixtures thereof.

One suitable hydroxypropylmethylcellulose compound is "HPMC 2910", which is a cellulose ether having a degree of substitution of about 1.9 and a hydroxypropyl molar substitution of 0.23, and containing, based upon the total weight of the compound, from about 29% to about 30% methoxyl and from about 7% to about 12% hydroxylpropyl groups. As used herein, "degree of substitution" shall mean the average number of substituent groups attached to an anhydroglucose ring, and "hydroxypropyl molar substitution" shall mean the number of moles of hydroxypropyl per mole anhydroglucose. HPMC 2910 is commercially available from the Dow Chemical Company under the tradename, "Methocel E."

"Methocel E5," which is one grade of HPMC-2910 suitable for use in the present invention, has a viscosity of about 4 to 6 cps (4 to 6 millipascal-seconds) at 20° C. in a 2% aqueous solution as determined by a Ubbelohde viscometer. Similarly, "Methocel E6," which is another grade of HPMC-2910 suitable for use in the present invention, has a viscosity of about 5 to 7 cps (5 to 7 millipascal-seconds) at 20° C. in a 2% aqueous solution as determined by a Ubbelohde viscometer. "Methocel E15," which is another grade of HPMC-2910 suitable for use in the present invention, has a viscosity of about 15000 cps (15 millipascal-seconds) at 20° C. in a 2% aqueous solution as determined by a Ubbelohde viscometer.

One suitable polyvinyl alcohol and polyethylene glycol copolymer is commercially available from BASF Corporation under the tradename "Kollicoat IR".

As used herein, "modified starches" include starches that have been modified via crosslinking and/or other chemical modification for improved stability or optimized performance, or physical modification for improved solubility properties or optimized performance. Examples of chemically-modified starches are well known in the art and typically include those starches that have been chemically treated to cause replacement of some of its hydroxyl groups with either ester or ether groups. Crosslinking, as used herein, may occur in modified starches when two hydroxyl groups on neighboring starch molecules are chemically linked. As used herein, "pre-gelatinized starches" or "instantized starches" refers to physically modified starches that have been pre-wetted, then dried to enhance their cold-water solubility. Suitable modified starches are commercially available from several suppliers such as, for example, A.E. Staley Manufacturing Company, and National Starch & Chemical Company.

A suitable film forming modified starch includes the pre-gelatinized waxy maize derivative starches that are commercially available from National Starch & Chemical Company under the tradenames, "Purity Gum" and "FilmSet", and derivatives, copolymers, and mixtures thereof. Such waxy maize starches typically contain, based upon the total weight of the starch, from about 0 percent to about 18 percent of amylose and from about 100 percent to about 88 percent of amylopectin.

Another suitable film forming modified starch includes the hydroxypropylated starches, in which some of the hydroxyl groups of the starch have been etherified with hydroxypropyl groups, usually via treatment with propylene oxide. One example of a suitable hydroxypropyl starch that possesses film-forming properties is available from Grain Processing Company under the tradename, "Pure-Cote B790".

Suitable film forming tapioca dextrins include those available from National Starch & Chemical Company under the tradename, "Crystal Gum" or "K-4484," and derivatives thereof such as modified food starch derived from tapioca, which is available from National Starch and Chemical under the tradename, "Purity Gum 40," and copolymers and mixtures thereof.

Another suitable film forming material derived from starch is corn syrup solids, which is commercially available from National Starch and Chemical under the trademark, "N-Tack"; derivatives thereof; copolymers thereof; and mixtures thereof.

Any gelling polymer known in the art is suitable for use in the present invention. Examples of such gelling polymers include but are not limited to hydrocolloids such as alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, whelan, rhamsan, zooglan, methylan, chitin, chitosan; gelling starches such as acid hydrolyzed starches and derivatives and mixtures thereof.

Suitable xanthan gums include those available from C.P. Kelco Company under the tradename, "Keltrol 1000," "Xantrol 180," or "K9B310."

"Gelling starches," as used herein, include those starches that, when combined with water and heated to a temperature sufficient to form a solution, thereafter form a gel upon cooling to a temperature below the gelation point of the starch. Examples of gelling starches include, but are not limited to, acid hydrolyzed starches such as that available from Grain Processing Corporation under the tradename, "Pure-Set B950"; hydroxypropyl distarch phosphate such as that available from Grain Processing Corporation under the tradename, "Pure-Gel B990", and mixtures thereof.

"Acid-hydrolyzed starch," as used herein, is one type of modified starch that results from treating a starch suspension with dilute acid at a temperature below the gelatinization point of the starch. During the acid hydrolysis, the granular form of the starch is maintained in the starch suspension, and the hydrolysis reaction is ended by neutralization, filtration and drying once the desired degree of hydrolysis is reached. As a result, the average molecular size of the starch polymers is reduced. Acid-hydrolyzed starches (also known as "thin boiling starches") tend to have a much lower hot viscosity than the same native starch as well as a strong tendency to gel when cooled.

Any adhesive polymer known in the art is suitable for use in the present invention. Examples of such adhesive polymers include, but are not limited to, polysaccharides such as maltodextrin, polydextrose, and mucilagee; proteins such as gelatin, whey protein, and albumin, and derivatives and combinations thereof.

Examples of solvents suitable for use in the present invention include, but are not limited to, water; water-miscible polar organic solvents such as methanol, ethanol, isopropanol, and acetone; non-water miscible organic solvents such as methylene chloride, methylethylketone, methylisobutylketone, chloraform, benzene, toluene, pentane, and hexane; and derivatives and mixtures thereof.

In one embodiment, the polymer dispersion is substantially free of adjuvants or modifiers such as plasticizers, dispersion aids, wetting agents, stabilizers, preservatives, and the like. By substantially free, it is meant that the polymer dispersion contains, based upon the total weight of the polymer dispersion, less than about 5%, e.g. less than about 1% of adjuvants or modifiers.

The polymeric dispersion may be prepared by dispersing the dispersable polymer in the solvent under suitable conditions to uniformly disperse the polymer at the molecular level. In one embodiment wherein the solvent is water, the polymeric dispersion may be prepared by heating water to a temperature effective for solubilizing the polymer. Although the temperature and quantity of water may depend on, for example, the solubility of the polymer selected, typically the required temperature may range from about room temperature to about 90° C. The dispersible polymer may then be added to the heated water, with stirring, until all of the polymer is dissolved therein. The resulting solution is cooled to ambient temperature and, if necessary, further diluted with an additional amount of room temperature water in order to achieve the desired solution concentration.

The polymeric dispersion of the present invention may be applied to various types of substrates, especially those that are soft and/or are highly friable. Examples of such treated substrates may nonexclusively result products such as pharmaceutical dosage forms, confectionary products, nutritional supplements, food stuffs, dyestuffs, and dietary supplements In accordance with the present invention, an effective amount of the polymeric dispersion of the present invention may be applied to the surface of the substrate such that the overall friability of the treated substrate is reduced by a factor of at least about 2, e.g. at least about 2.5, at least about 3, or at least about 5, relative to the friability of the uncoated substrate. Such a reduction in friability may be achieved by applying the composition of the present invention to at least a portion of a vulnerable edge such that less than all of the exterior substrate surface, e.g. from about 10% to about 90%, from about 20% to about 80% or from about 20% to about 50% of the exterior substrate surface, has been treated with the polymeric dispersion.

In one embodiment, the polymeric dispersion is primarily applied to at least a portion of: 1) one or more of the rims; 2) the belly band; 3) one or more of the face(s); 4) and/or one or more of the land(s), with the remainder of the substrate having no polymeric dispersion applied thereto.

The areas of a flat, disk-shaped tablet onto which a polymeric dispersion may be applied are illustrated in FIGS. 7A through 7E, and further explained in Table A below:

TABLE A

Areas For Polymeric Dispersion Application

| FIG. NO. | AREAS ON TABLET TO WHICH DISPERSION IS APPLIED |
|---|---|
| 7A | Two faces (including two rims) |
| 7B | Belly band (including two rims) |
| 7C | Two faces (including one-half of a rim/face) |
| 7D | Belly band (including one-half of an upper rim and one-half of a lower rim) |
| 7E | Two rims |

When the polymeric dispersion is applied to a vulnerable edge on the substrate, the resulting treatment area includes both that vulnerable edge as well as an overlap area. Hence, the quantity of substrate surface area receiving treatment may be approximated by relating about 1 linear millimeter of vulnerable edge to about 2 square millimeters of treated substrate surface. See, for example, FIG. 2, which exemplifies that treatment of the rim includes an overlap area 15. For substrates that do not bear substantial opposing planar surfaces, such as, for example, the biconvex shape of FIG. 5, the polymeric dispersion may be applied on the upper land 43' and/or the lower land 43" in a similar fashion such that an effective amount of the dispersion enrobes and includes one-half of the upper rim 41' and/or one-half of the lower rim 41", respectively, in an overlap area 115.

One skilled in the art may readily appreciate that the location and size of the substrate surface area on which the polymeric dispersion treatment is applied may vary depending upon, for example, the nature of the substrate surface, the thickness of the polymeric dispersion application, the shape of the substrate, and the dimensions of the substrate.

The quantity of polymeric dispersion applied to the substrate will depend upon a number of factors including, but not limited to, the concentration of the polymer in the dispersion, the desired thickness of the application on the substrate, the hardness of the substrate surface, and the dimension of the substrate surfaces. However, in order to obtain a friability reduction factor (as defined in Table B) of at least about 2, the polymeric dispersion should be applied to at least one treatment surface location such that the substrate possesses a polymer layer of from about 3 micrograms/mm$^2$ to about 20 micrograms/mm$^2$, e.g. from about 4 micrograms/mm$^2$ to about 12 micrograms/mm$^2$ or from about 5 micrograms/mm$^2$ to about 9 micrograms/mm$^2$.

The composition of the present invention may be applied to a substrate by any method well known in the art. Such methods may include, but are not limited to, the use of a wet roller, a brush, or a spray nozzle, and are disclosed in, for example, U.S. Pat. No. 5,922,342, which is incorporated by reference herein In one embodiment, the substrate may be removably secured to a rotation means, and the polymeric dispersion may then be applied to the desired treatment surface location on the rotating substrate.

Although the temperature and pressure conditions for applying the polymeric dispersion to the substrate will vary dependent upon several factors such as, for example, the type of polymers selected, in general the temperature may range from about 20° C. to about 90° C., e.g. from about 25° C. to 65° C. For example, in polymeric dispersions containing HPMC, the polymeric dispersion is generally applied to the substrate at a temperature of less than about 90° C. because HPMC is not soluble in water at higher temperatures.

After the polymeric dispersion is applied to the desired treatment surface on the substrate, the treated substrate may then be dried in order to evaporate the solvent from the composition and to set the polymer. The desired drying temperature and setting time may vary depending upon, for example, the type of polymer selected, the solvent employed, and the concentration of polymeric dispersion employed, and would readily be appreciated by one having ordinary skill in the art without undue experimentation.

Figure 8A:
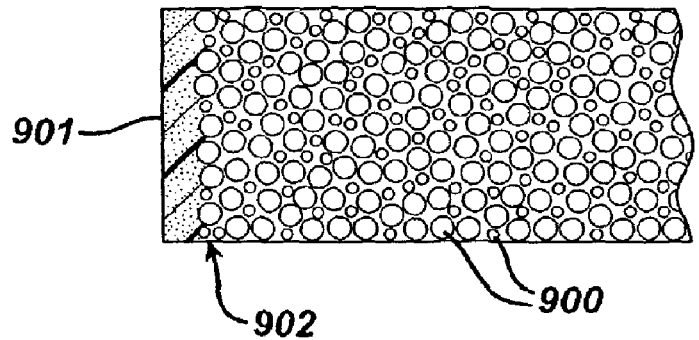
FIG. 8A is an enlarged, cross-sectional view of a substrate having a polymeric layer residing upon at least a portion of its treatable surface.
Figure 8B:
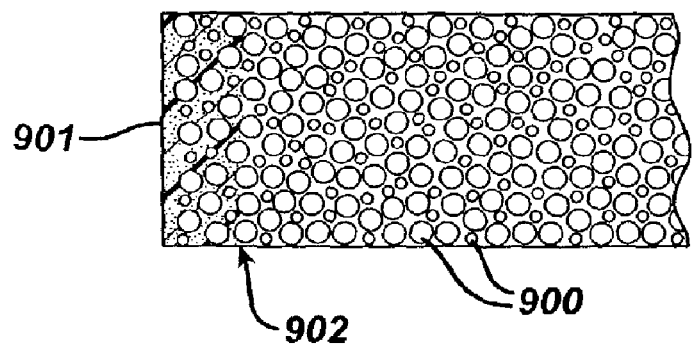
FIG. 8B is an enlarged, cross-sectional view of a substrate having a polymeric layer residing at least a portion of its treatable surface.
Figure 8C:
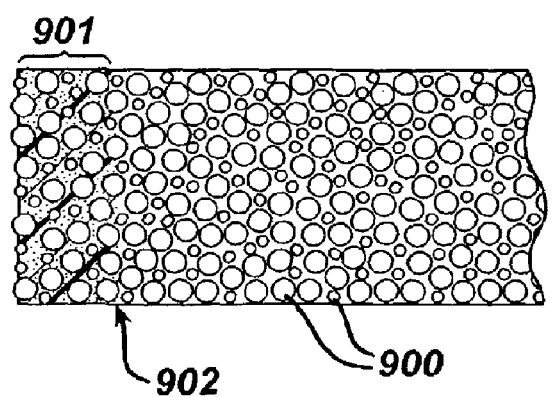
FIG. 8C is an enlarged, cross-sectional view of a substrate having a polymeric layer residing immediately beneath at least a portion of its treatable surface.

The treated substrate produced in accordance with the present invention possesses a polymeric layer that is in contact with the treatable surface of the substrate. As used herein, "in contact with" shall mean that the layer resides upon, and/or resides at, and/or resides immediately beneath, at least a portion of the treatable surface, and "immediately beneath," as used herein shall mean within a location that is less than about 2 mm inwards from the treatable surface. For example, the polymeric dispersion may penetrate the treatable surface to the extent that the formed polymer layer both resides immediately beneath the treatable surface as well as at the treatable surface. FIG. 8A represents a cross-sectional view of a substrate 900 possessing a polymeric layer 901 that resides upon at least a portion of the treatable surface 902. FIG. 8B represents a cross-sectional view of a substrate 900 possessing a polymeric layer 901 residing at a portion of the treatable surface 902. FIG. 8C is a cross-sectional view of a substrate 900 possessing a polymeric layer 901 immediately beneath at least a portion of the treatable surface 902. The depth of penetration of the applied polymeric dispersion may depend upon a number of factors such as, for example, the hardness of the substrate.

Advantageously, substrates treated with polymeric dispersions in accordance with the present invention do not incur an increase in hardness that is substantially perceptible to the user. In addition, such treated substrates incur a negligible weight gain, i.e., e.g., a post-drying gain of less than about 0.5%. In one embodiment, the weight of the water dispersible polymer layer is not more than about 0.5%, e.g. not more than about 0.25%, say not more than about 0.1% of the weight of the untreated substrate.

Surprisingly, we have also found that when the polymeric dispersion is applied predominantly to the treatable surfaces, so that from about 10% to about 90% of the overall substrate surface has been treated with the polymeric dispersion of the present invention, the overall friability of the substrate is reduced by a factor of at least about 2. Because a consumer would not perceive the addition of the small quantity of composition thereto, this reduction in friability occurs without a sacrifice in organoleptic characteristics, such as mouthfeel. In one embodiment, the tablets of the present invention posses a fast melt-away charasteric because their disintegration and dissolution in the oral cavity are not hindered by the presence of a coating.

Another substantial advantage of this invention is that it permits low hardness substrates to be subsequently coated with one or more additional coatings (e.g. film-coatings) using processes that may have otherwise destroyed the integrity of such substrates but for the treatment in accordance with the present invention.

Yet another substantial advantage of this invention is apparent in the use of the polymeric dispersion in immediate release dosage forms. More specifically, because the polymeric dispersion is water dispersible, a reduction in friability of the substrate can be achieved without detriment to its immediate release properties of the substrate.

The invention illustratively disclosed herein suitably may be practiced in the absence of any component, ingredient, or step that is not specifically disclosed herein. An example is set forth below to further illustrate the nature of the invention and the manner of carrying it out. However, the invention should not be considered as being limited to the details thereof.

EXAMPLES

Example 1

Preparation HPMC Surface Treatment Solution

A surface treatment solution having the components set forth below was prepared as follows:
Coating Solution Ingredients:

| | |
|---|---|
| Deionized water | 100 mL |
| HPMC* | 5.0 g |

*Methocel HPMC E5" available from Dow Corning.

30 mL of deionized water was placed into a beaker and heated to 90° C. on a hot plate. After adding 5.0 grams of HPMC powder thereto, with stirring and under constant temperature, 50 mL of deionized water, having a temperature of 25° C., was then added thereto with stirring until all of the HPMC was dissolved. The resulting solution was then diluted to volume with deionized water at room temperature in a 100 mL volumetric flask.

Example 2

Application of HPMC Surface Treatment Solution to Substrate Rims

A round, flat-faced, beveled edge tablet, which was commercially available from McNEIL-PPC, Inc. under the tradename, "MOTRIN Jr. Strength," was selected from a batch with an average hardness value of 2.57 kp/cm$^2$. The tablet, which had a height of approximately 5.56 mm and a radius of approximately 12 mm, weighed about 770 mg. The tablet was fixed to a ¼ inch wooden dowel attached to an inverted mixer (Model RW-20 DZM, Janke&Kunkel, IKA-Works, Inc.) with a small quantity of mounting putty (Manco Inc.). The mixer was set to rotate the dowel and substrate at approximately 30 rpm.

An artist's brush having a total bristle width of approximately 3 mm was wetted with the solution of Example 1 and applied continuously to the tablet rims while the substrate rotated. The wet weight gain of applied solution was approximately 8.7 mg, which yielded a dry weight gain of approximately 0.44 mg HPMC. The tablet was then inverted and the same solution was applied to the opposing rim in a similar manner. The tablet was then permitted to dry at room temperature for 24 hours.

This procedure was independently repeated on 14 additional tablets.

Example 3

Application of HPMC Surface Treatment Solution to Substrate Bellyband

The procedure set forth in Example 2 was independently repeated on 10 tablets, but with treatment of the belly band as opposed to the rim of each tablet.

Example 4

Application of HPMC Surface Treatment Solution to Substrate Faces

The procedure set forth in Example 2 was independently repeated on 10 tablets, but with treatment of both opposing faces as opposed to the rim of each tablet.

Example 5

Comparative Friability

The treated tablets prepared in accordance with Examples 2-4, along with one control group of 10 tablets that had about 15 μg of deionized water applied to each of their opposing faces, and a second control group of 10 tablets which were entirely untreated, were tested for friability using the rotating drop method of United States Pharmacopeia Chapter <1216> (1995). The results are shown in Table B below:

TABLE B

Friability Comparison Using USP Chapter <1216>

| Tablets (round, flat-faced, beveled edge) 770 mg, hardness value (n = 5) | Treatment Solution | Treatment Surface | Friability | Friability Factor* |
|---|---|---|---|---|
| 2.57 kp/cm$^2$ | Water | both faces | 3.75% | 2.2 |
| | 5% HPMC | both faces (Ex. 4) | 0.46% | 18 |
| | 5% HPMC | Bellyband (Ex. 3) | 1.72% | 4.8 |
| | 5% HPMC | Rim (Ex. 2) | 0.16% | 51.8 |
| | Control (10 tablets) | none | 8.28% | 1 |

*Friability Factor is defined as (friability of the control, uncoated substrate)/(friability of the coated substrate).

This Example demonstrated that treating a soft substrate with the composition of the present invention at predominantly only the rim of the substrate surface substantially improved the friability of the treated tablets. In particular, this Example showed that the friability of tablets, which were treated only along the rim, was significantly lower that that of the tablets which were treated on both faces.

Example 6

Preparation of an N-Tack Starch Surface Treatment Solution

A surface treatment solution having the components set forth below was prepared as follows:
Coating Solution Ingredients:

| | |
|---|---|
| Deionized water | 100 mL |
| N-Tack Starch* | 25.0 g |

*N-Tack Starch available from National Starch & Chemical Company.

70 mL of deionized water was placed into a beaker and heated to 70° C. on a hot plate. Then 25.0 grams of N-Tack corn syrup solids were added thereto, with stirring until all of the corn syrup solids were dissolved. The resulting solution was diluted to volume with deionized water at room temperature in a 100 mL volumetric flask.

Example 7

Determination of Treatment Surface Size

The polymeric dispersion of Example 1 was applied to 15 untreated tablets of Example 2 ($^{15}/_{32}$" diameter, 5.56 mm height) in accordance with the procedure set forth in Examples 2-4. For each tablet, the polymeric dispersion (6.7 μg per mm$^2$ of surface treated) was applied to one of the treatment surfaces identified in FIG. 7A through FIG. 7E. The treated surface area, which was expressed in terms of the percentage of total substrate surface area that was treated with the polymeric dispersion, was measured.

This procedure is repeated for the tablets having a ¼" diameter and a ¾" diameter, respectively. Table C below shows the measured results for the treated tablets:

TABLE C

Treated Surface Area in terms of Total Tablet Surface Area

| Treatment Surface | Tablet w/¼" diameter, 2.8 mm height | Tablet w/$^{15}/_{32}$" diameter, 5.56 mm height | Tablet w/¾" diameter, 9 mm height |
|---|---|---|---|
| Both faces (FIG. 7A) | 86.6% | 66.2% | 61.4% |
| Belly Band and both rims* (FIG. 7B) | 76.4% | 64.2% | 60.0% |
| Both faces, ½ upper rim and ½ lower rim (FIG. 7C) | 52.3% | 51.7% | 50.4% |
| Bellyband, ½ upper rim and ½ lower rim (FIG. 7D) | 47.7% | 48.3% | 49.6% |
| Both rims (FIG. 7E) | 63.0% | 30.4% | 21.4% |

*Overlap area was 1 mm

This example shows that the percentage of coating varies depending upon the coating location and the dimensions of the tablet; however in general, the treated coating surface ranges from about 10% to about 90% of the total exterior substrate surface area.

Example 8

Friability Factor of Substrates

A. Preparation of Chewable Tablets

Ibuprofen particles coated with a mixture of hydroxyethylcellulose and hydroxypropylmethylcellulose, according to the method disclosed in U.S. Pat. No. 5,320,855 were blended with aspartame, prosweet powder, citric acid, granular mannitol, microcrystalline cellulose, flavor and color in a plastic bag by inverting about 100 times. After magnesium stearate was added thereto, the mixture was further blended by inverting about 20 times. The components of the resulting blend are set forth in Table C below:

TABLE C

Components of Chewable Blend

| Component Name | Amount Used (mg/tablet) |
|---|---|
| Encapsulated Ibuprofen (76.25%) | 131.14 |
| Aspartame** | 10.82 |
| Prosweet Powder No. 694* | 2.54 |
| Citric Acid** | 4.26 |
| Mannitol** | 528.10 |
| Microcrystalline cellulose*** | 84.10 |
| FD&C Yellow No. 6 Aluminum Lake | 1.76 |
| Orange flavor** | 1.76 |
| Magnesium stearate** | 5.52 |
| TOTAL | 770 |

*available from the Virginia Dare Company of Brooklyn, NY.
**These components are readily available and may be commercially purchased from any of the suppliers set forth in the "Handbook of Pharmaceutical Excipients ($2^{nd}$ Ed. 1994).
***available from FMC Corporation under the tradename, "AVICEL PH101;"

The resulting blend was then compressed on a rotary tablet press at 40 rpm using $^{15}/_{32}$" diameter flat faced beveled edge tablet tooling to yield tablets having an average tablet weight of 770 mg. Compression force was adjusted to yield final tablets possessing a hardness value of 7.92 kp/cm$^2$.

This procedure was repeated to with lower compression force to yield 10 additional tablets having a hardness value of 5.89 kp/cm$^2$ and 10 additional tablets having a hardness value of 2.57 kp/cm$^2$.

10 of the tablets having a hardness value of 7.92 kp/cm$^2$ were then treated with a 5% HPMC polymeric dispersion produced in Example 1 at both faces in accordance with the procedure set forth in Example 4 above. Similarly, additional tablets were independently treated in accordance with the procedures set forth in Examples 2-4 and the various treatments solutions and treatment surface criteria set forth in Table D below:

TABLE D

Friability of Substrates

| Tablets (round, flat-faced, beveled edge) 770 mg, hardness value (n = 5) | Treatment Solution (# of tablets treated)*** | Treatment Surface | Friability (%) | Friability Factor** (vs. control) |
|---|---|---|---|---|
| 7.92 kp/cm$^2$ | 5% HPMC (10) | both faces | 0.01 | 124 |
|  | 4% HPMC (10) | both faces | 0.34 | 3.65 |
|  | 3% HPMC (10) | both faces | 0.43 | 2.88 |
|  | Control* (10) | none | 1.24 | 1.00 |
| 5.89 kp/cm$^2$ | Water (10) | both faces | 2.37 | 1.13 |
|  | 5% HPMC (10) | both faces | 0.12 | 22.3 |
|  | 4% HPMC (10) | both faces | 0.43 | 6.23 |
|  | 3% HPMC (10) | both faces | 1.28 | 2.09 |
|  | 5% HPMC (10) | bellyband | 0.56 | 4.79 |
|  | 5% HPMC (10) | rim | 0.10 | 26.8 |
|  | Control* (10) | none | 2.68 | 1.00 |

TABLE D-continued

Friability of Substrates

| Tablets (round, flat-faced, beveled edge) 770 mg, hardness value (n = 5) | Treatment Solution (# of tablets treated)*** | Treatment Surface | Friability (%) | Friability Factor** (vs. control) |
|---|---|---|---|---|
| 2.57 kp/cm² | Water (10) | both faces | 3.75 | |
| | 5% HPMC (10) | both faces | 0.46 | 18.0 |
| | 4% HPMC (10) | both faces | 0.37 | 22.4 |
| | 3% HPMC (10) | both faces | 1.96 | 4.22 |
| | 5% HPMC (10) | bellyband | 1.72 | 4.81 |
| | 5% HPMC (10) | rim | 0.16 | 51.8 |
| | 4% Maltodextrin (10) | both faces | 3.77 | 2.20 |
| | 2% Pullulan (10) | both faces | 2.06 | 4.02 |
| | 4% Pullulan (10) | both faces | 0.57 | 14.5 |
| | 4% Pullulan (10) | whole tablet | 0.78 | 10.6 |
| | 4% N-Tack ® (10) | both faces | 2.67 | 3.10 |
| | 10% N-Tack ® (10) | both faces | 0.73 | 11.3 |
| | 25% N-Tack ® (10) | both faces | 0.26 | 31.8 |
| | 4% Gelatin (10) | both faces | 0.63 | 13.1 |
| | Control* (10) | none | 8.28 | 1.00 |

*Friability of control is average friability of ten (10) uncoated tablets
**Friability Factor is defined as (friability of the control, uncoated substrate)/(friability of the coated substrate).
***The N-Tack ®-containing dispersion was produced in accordance with the procedure set forth in Example 6, but with varying the amount of the N-Tack ®. The pullulan, gelatin, and maltodextrin dispersions were independently prepared in accordance with the procedure set forth in Example 1, but with the substitution of pullulan, gelatin, and maltodextrin, respectively, for the HPMC, and with variation of the amount of the polymer.

This Example showed that the friability of the treated substrates was significantly reduced by applying the polymeric dispersion to only a portion of the substrate surface. The effectiveness of the treatment depends on the water dispersible polymer employed, the substrate hardness, and the location of treatment surface. For example, the largest friability factors (most reduction in friability) were obtained by applying a 5% HPMC dispersion to both faces of the hardest tablet, and by applying a 25% corn syrup solids dispersion to both faces of the softest tablet.

We claim:

1. A method of administering a pharmaceutical active ingredient, said method comprising chewing a treated pharmaceutical substrate comprising said pharmaceutical active ingredient, wherein said treated pharmaceutical substrate comprises a soft pharmaceutical substrate having a hardness value of from about 1 kp/cm2 to about 5 kp/cm2 wherein at least a portion of the exterior surface of said soft pharmaceutical substrate is in contact with a pharmaceutically-acceptable, water dispersible polymer layer to form a treated surface, wherein (i) the surface area of said treated surface includes at least a portion of a vulnerable edge, based upon the total surface area of the exterior surface, from about 10% to about 90%, (ii) the treated pharmaceutical substrate contains from about 3 µg to about 20 µg of polymer per square millimeter of treated surface, and (iii) the treated pharmaceutical substrate possesses immediate release properties and a friability reduction factor of at least about 2.

2. The method of claim 1 wherein the treated pharmaceutical substrate contains from about 5 µg to about 9 µg of polymer per square millimeter of treated surface.

3. The method of claim 1 wherein the surface area of the treated surface is, based upon the total surface area of the exterior surface, from about 20% to about 50%.

4. The method of claim 2 wherein the surface area of the treated surface is, based upon the total surface area of the exterior surface, from about 20% to about 50%.

5. The method of claim 1 wherein the treated pharmaceutical substrate has a hardness value of no more than about 5 kp/cm².

6. The method of claim 1 having a friability reduction factor of at least about 3.

7. The method of claim 1 having a friability reduction factor of at least about 5.

8. The method of claim 1, wherein the polymeric dispersion is comprised of film forming polymers, gelling polymers, adhesive polymers, and derivatives, copolymers, and mixtures thereof.

9. The method of claim 8, wherein in the polymeric dispersion is comprised of polyvinylalcohol (PVA), hydroxypropyl starch, hydroxyethyl starch, pullulan, methylethyl starch, carboxymethyl starch, methylcellulose, hydroxypropylcellulose (HPC), hydroxyethylmethylcellulose (HEMC), hydroxypropylmethylcellulose (HPMC), hydroxybutylmethylcellulose (HBMC), hydroxyethylethylcellulose (HEEC), hydroxyethylhydroxypropylmethyl cellulose (HEMPMC), methacrylic acid copolymers, methacrylate ester copolymers, polyvinyl alcohol and polyethylene glycol copolymers, proteins, pre-gelatinized starches, corn syrup solids, film-forming modified starches, and copolymers, derivatives and mixtures thereof.

10. The method of claim 9, wherein the polymeric dispersion comprises at least one polymer selected from the group consisting of hydroxypropylmethylcellulose, hydroxypropylcellulose, polyvinyl alcohol and polyethylene glycol copolymer hydroxypropyl starch, corn syrup solids, maltodextrin, pullulan, gelatin, and tapioca dextrin and copolymers, derivatives and mixtures thereof.

11. The method of claim 1, wherein the soft pharmaceutical substrate contains an active agent selected from the group consisting of acetaminophen, ibuprofen, pseudoephedrine, famotidine, or pharmaceutically acceptable salts thereof, and mixtures thereof.

12. The method of claim 1, wherein the treated surface is a first land having a first surface and a second land having a second surface, and the polymeric layer is in contact with at least a portion of said first surface and/or said second surface.

13. The method of claim 1, wherein the treated surface is a rim having a rim surface, and the polymeric layer is in contact with at least a portion of the rim surface.

14. The method of claim 1, wherein the treated surface is bellyband having a bellyband surface, and the polymeric layer is in contact with at least a portion of said bellyband surface.

15. The method of claim 1, wherein the treated surface is a face having a face surface, and the polymeric layer is in contact with at least a portion of said face surface.

16. A method of administering a pharmaceutical active ingredient, said method comprising chewing a treated pharmaceutical substrate comprising said pharmaceutical active ingredient, wherein said treated pharmaceutical substrate is comprised of: a) a soft pharmaceutical substrate having a hardness value of from about 1 kp/cm2 to about 5 kp/cm2 and comprised of an exterior surface; and b) a pharmaceutically-acceptable, water dispersible polymer layer in contact with at least a portion of said exterior surface to form a treated surface, wherein the surface area of said treated surface includes at least a portion of a vulnerable edge, based upon the total surface area of the exterior surface, from about 10% to about 90%, the weight of said water dispersible polymer layer is not more than about 0.5% of the weight of the untreated substrate, and the treated pharmaceutical substrate possesses immediate release properties and a friability reduction factor of at least about 2.

17. The method of claim 16 wherein the treated pharmaceutical substrate contains from about 3 µg to about 20 µg of polymer per square millimeter of treated surface.

18. The method of claim 16 wherein the treated pharmaceutical substrate contains from about 5 µg to about 9 µg of polymer per square millimeter of treated surface.

19. The method of claim 16 wherein the surface area of the treated surface is, based upon the total surface area of the exterior surface, from about 20% to about 50%.

* * * * *